United States Patent
Chen et al.

(10) Patent No.: US 11,371,058 B2
(45) Date of Patent: Jun. 28, 2022

(54) MAIZE PARTHENOGENETIC HAPLOID-INDUCING GENE ZMPLA1E AND APPLICATION THEREOF

(71) Applicant: CHINA AGRICULTURAL UNIVERSITY, Beijing (CN)

(72) Inventors: Shaojiang Chen, Beijing (CN); Yu Zhong, Beijing (CN); Chenxu Liu, Beijing (CN)

(73) Assignee: CHINA AGRICULTURAL UNIVERSITY, Beijing (CN)

( * ) Notice: Subject to any disclaimer, the term of this patent is extended or adjusted under 35 U.S.C. 154(b) by 88 days.

(21) Appl. No.: 16/652,005

(22) PCT Filed: Dec. 19, 2018

(86) PCT No.: PCT/CN2018/121993
§ 371 (c)(1),
(2) Date: Mar. 27, 2020

(87) PCT Pub. No.: WO2019/153899
PCT Pub. Date: Aug. 15, 2019

(65) Prior Publication Data
US 2020/0347402 A1    Nov. 5, 2020

(30) Foreign Application Priority Data
Feb. 8, 2018 (CN) .......................... 201810129251.8

(51) Int. Cl.
*C12N 15/82* (2006.01)
*C07K 14/415* (2006.01)

(52) U.S. Cl.
CPC ........ *C12N 15/8287* (2013.01); *C07K 14/415* (2013.01); *C12N 15/8213* (2013.01); *C12N 15/8218* (2013.01)

(58) Field of Classification Search
CPC ............ C12N 15/8287; C12N 15/8213; C12N 15/8218
See application file for complete search history.

(56) References Cited

FOREIGN PATENT DOCUMENTS

| CN | 101377481 | 3/2009 |
| CN | 102440179 | 5/2012 |

OTHER PUBLICATIONS

Liu, Chenxu, et al. "A 4-bp insertion at ZmPLA1 encoding a putative phospholipase A generates haploid induction in maize." Molecular plant 10.3 (2017): 520-522. (Year: 2017).*
Sarkar, K. R., and E. H. Coe Jr. "A genetic analysis of the origin of maternal haploids in maize." Genetics 54.2 (1966): 453 (Year: 1966).*
Chalyk, S. T. "Properties of maternal haploid maize plants and potential application to maize breeding." Euphytica 79.1 (1994): 13-18. (Year: 1994).*
First Office Action issued in corresponding Chinese Application No. 201811554223.7; dated May 13, 2020; 13 pgs.
Second Office Action issued in corresponding Chinese Application No. 201811554223.7; dated Jan. 20, 2021; 10 pgs.
*Zea mays* DUF679 domain membrane protein 7 (LOC100277972), mRNA; NCBI Reference Sequence: NM_001151404.2; GenBank; Sep. 7, 2017; 2 pgs.
International search report dated Mar. 21, 2019 from corresponding application No. PCT/CN2018/121993.
Kelliher et al, "MATRILINEAL, a sperm-specific phospholipase, triggers maize haploid induction", Nature, vol. vol. 542, Jan. 23, 2017 (Jan. 23, 2017), Total 18 pages.
Alexandrov. N.N. et al. "Registry No. NP_001144876.2", GenBank, Sep. 7, 2017 (Sep. 7, 2017),Total 2 pages.
Third Office Action issued in corresponding Chinese Application No. 201811554223.7; dated Jun. 7, 2021; 14 pgs.

* cited by examiner

*Primary Examiner* — Weihua Fan
(74) *Attorney, Agent, or Firm* — Hauptman Ham, LLP

(57) ABSTRACT

The present invention discloses a maize parthenogenetic haploid-inducing gene ZmPLA1E and application thereof. The present invention utilizes the method of exchanged individual plant progeny tests for the first time, and successfully proves that the ZmPLA1E gene can generate and significantly increase the parthenogenetic haploid induction ability in the process of self-crossing or hybridizing as a male parent with other maize materials after the ZmPLA1E gene is mutated in the coding region. The haploid-inducing gene ZmPLA1E of the present invention is important for the cultivation of high-frequency parthenogenetic haploid inducing lines and the application of haploid technology.

14 Claims, 3 Drawing Sheets
Specification includes a Sequence Listing.

SEQUENCE LISTING

<160> NUMBER OF SEQ ID NOS: 44

<210> SEQ ID NO 1
<211> LENGTH: 1061
<212> TYPE: DNA
<213> ORGANISM: Artificial Sequence
<220> FEATURE:
<223> OTHER INFORMATION: Synthesized

<400> SEQUENCE: 1

| | | | | | |
|---|---|---|---|---|---|
| aaaccaacag | ctttgcattt | ccagtctctg | ggaacgtcgc | gaaaacagtt | ccacgctctc | 60 |
| cggacaagaa | cgcgcccatg | gatcgcagca | acgccggtgc | ggtgtccgtc | gaggtgcgcg | 120 |
| gcggcggcgg | cggctcgccg | ccgggcgcgg | gaaggaagcg | ccgcgcgtg | gcgaggggcg | 180 |
| tgcagaagac | gctctccaag | acgtccatgc | tggccaactt | cctccccacg | ggcacgctgc | 240 |
| taaccttcga | gatgctactc | ccggccgccg | caggcgacgg | cacctgctcg | gcggtcagcg | 300 |
| ccgcgatgct | cagggccctg | ctcgcgctct | gcgccgcctc | ctgcttcctc | ttccacttca | 360 |
| ccgacagctt | ccgcgccccg | gacgggaagg | tgtactacgg | cttcgtcacg | ccgcggggcc | 420 |
| tgtcgctgtt | caggaccggg | ctcggcgtcg | aggtgcccag | ggaggaaagg | taccggctcg | 480 |
| ccttcgtcga | cgtcgtgcac | gctgtcatgt | ccgtgctggt | ctttgcggcc | gtcacgctcg | 540 |
| ccgactaccg | ggtctccggg | tgcctcgtcg | ccggccaccg | caaggagatg | gacgaggtga | 600 |
| tggagagctt | cccgctcatg | gtgggcgccg | tgtgcagcgg | cctcttcctc | ttgttcccca | 660 |
| acacccgcta | cggcatcggt | tgtttggctc | cgtaaaaaac | agcagactgg | aacagagagt | 720 |
| acggcagtgt | aactttcttc | cgtacctgtg | aatctggctt | gatcatttta | tgcttcatgt | 780 |
| tttcttagca | actgtaaaaa | cttggatgtg | atgtgatcct | atctttaatc | agtaccgatt | 840 |
| tgaaatttct | tgagaatgga | ttatacaaga | gaatgaatgg | tcaccaaaaa | tagctttaca | 900 |
| tcagatgcaa | aatgcattcc | tttcaaaaga | atggtagact | ggctcaatct | atcctaacgt | 960 |
| aagctgccgc | ccatgtatcc | tacattctgg | caagatacta | gtattttaca | agccacacag | 1020 |
| taagcaaagc | agcactctcc | tacctaccca | aaaaaaaag | a | | 1061 |

<210> SEQ ID NO 2
<211> LENGTH: 1055
<212> TYPE: DNA
<213> ORGANISM: Artificial Sequence
<220> FEATURE:
<223> OTHER INFORMATION: Synthesized

<400> SEQUENCE: 2

| | | | | | |
|---|---|---|---|---|---|
| aaaccaacag | ctttgctttt | ccagtctctg | ggaacgtcgc | gaaaacagtt | ccacgctctc | 60 |
| cggacaagaa | cgcgcccatg | gatcgcagca | acgccggtgc | ggtgtccgtc | gaggtgcgcg | 120 |
| gcggcggcgg | cggctcgccg | ccaggcgcgg | gaaggaagcg | ccgcgcgtg | gcgaggggcg | 180 |
| tgcagaagac | gctctccaag | acgtccacgc | tggccaactt | cctccccacg | ggcacgctgc | 240 |
| taaccttcga | gatgctactc | ccggccgccg | caggcgacgg | cacctgctcg | gcggtcagcg | 300 |
| ccgcgatgct | cagggccctg | ctcgcgctct | gcgccacctc | ctgcttcctc | ttccacttca | 360 |
| ccgacagctt | ccgcgccccg | gacgggaagg | tgtactacgg | cttcgtcacg | ccgcggggcc | 420 |
| tgtcgctgtt | caggaccggg | ctcggcgtcg | aggtgcccag | ggaggaaagg | taccggctcg | 480 |
| ccttcgtcga | cgtcgtgcac | gctgtcatgt | ccgtgctggt | ctttgccgcc | gtcgcgctcg | 540 |
| ccgactaccg | ggtctccggg | tgcctcgtcg | ccggccaccg | caaggagatg | gacgaggtga | 600 |
| tggagagctt | cccgctcatg | gtgggcgccg | tgtgcagcgg | cctcttcctc | ttgttcccca | 660 |

```
acacccgcta cggcatcggt tgtttggctc cgtaaaaaac agcagactgg aacagagagt    720
acggcagtgt aactttcttc cgtacctgtg aatctggctt gatcatttta tgcttcatgt    780
tttcttagca actgtaaaaa cttggatgtg atgtgatcct atcttaatca gtaccgattt    840
gaaatttctt cagaatggat tatacaagag aatggccacc aaaaatagct ttacatcaga    900
tgcaaaatgc attcctttca aaagaatggt aagactggct caatctatcc taacgtaagc    960
tgctgccgat gtatcctaca ttatggcaag atactagtat tttacaagcg acacagtaag   1020
caaagcagca ctctcctacc tacccaaaaa aaaga                              1055
```

<210> SEQ ID NO 3
<211> LENGTH: 205
<212> TYPE: PRT
<213> ORGANISM: Artificial Sequence
<220> FEATURE:
<223> OTHER INFORMATION: Synthesized

<400> SEQUENCE: 3

Met Asp Arg Ser Asn Ala Gly Ala Val Ser Val Glu Val Arg Gly Gly
1               5                   10                  15

Gly Gly Gly Ser Pro Pro Gly Ala Gly Arg Lys Arg Arg Ala Val Ala
            20                  25                  30

Arg Gly Val Gln Lys Thr Leu Ser Lys Thr Ser Met Leu Ala Asn Phe
        35                  40                  45

Leu Pro Thr Gly Thr Leu Leu Thr Phe Glu Met Leu Leu Pro Ala Ala
    50                  55                  60

Ala Gly Asp Gly Thr Cys Ser Ala Val Ser Ala Met Leu Arg Ala
65                  70                  75                  80

Leu Leu Ala Leu Cys Ala Ala Ser Cys Phe Leu Phe His Phe Thr Asp
                85                  90                  95

Ser Phe Arg Ala Pro Asp Gly Lys Val Tyr Tyr Gly Phe Val Thr Pro
            100                 105                 110

Arg Gly Leu Ser Leu Phe Arg Thr Gly Leu Gly Val Glu Val Pro Arg
        115                 120                 125

Glu Glu Arg Tyr Arg Leu Ala Phe Val Asp Val His Ala Val Met
    130                 135                 140

Ser Val Leu Val Phe Ala Ala Val Thr Leu Ala Asp Tyr Arg Val Ser
145                 150                 155                 160

Gly Cys Leu Val Ala Gly His Arg Lys Glu Met Asp Glu Val Met Glu
                165                 170                 175

Ser Phe Pro Leu Met Val Gly Ala Val Cys Ser Gly Leu Phe Leu Leu
            180                 185                 190

Phe Pro Asn Thr Arg Tyr Gly Ile Gly Cys Leu Ala Pro
        195                 200                 205

<210> SEQ ID NO 4
<211> LENGTH: 205
<212> TYPE: PRT
<213> ORGANISM: Artificial Sequence
<220> FEATURE:
<223> OTHER INFORMATION: Synthesized

<400> SEQUENCE: 4

Met Asp Arg Ser Asn Ala Gly Ala Val Ser Val Glu Val Arg Gly Gly
1               5                   10                  15

Gly Gly Gly Ser Pro Pro Gly Ala Gly Arg Lys Arg Arg Ala Val Ala
            20                  25                  30

Arg Gly Val Gln Lys Thr Leu Ser Lys Thr Ser Thr Leu Ala Asn Phe
        35                  40                  45

Leu Pro Thr Gly Thr Leu Leu Thr Phe Glu Met Leu Leu Pro Ala Ala
    50                  55                  60

Ala Gly Asp Gly Thr Cys Ser Ala Val Ser Ala Ala Met Leu Arg Ala
65                  70                  75                  80

Leu Leu Ala Leu Cys Ala Thr Ser Cys Phe Leu Phe His Phe Thr Asp
                85                  90                  95

Ser Phe Arg Ala Pro Asp Gly Lys Val Tyr Tyr Gly Phe Val Thr Pro
            100                 105                 110

Arg Gly Leu Ser Leu Phe Arg Thr Gly Leu Gly Val Glu Val Pro Arg
        115                 120                 125

Glu Glu Arg Tyr Arg Leu Ala Phe Val Asp Val His Ala Val Met
    130                 135                 140

Ser Val Leu Val Phe Ala Ala Val Ala Leu Ala Asp Tyr Arg Val Ser
145                 150                 155                 160

Gly Cys Leu Val Ala Gly His Arg Lys Glu Met Asp Glu Val Met Glu
                165                 170                 175

Ser Phe Pro Leu Met Val Ala Ala Val Cys Ser Gly Leu Phe Leu Leu
            180                 185                 190

Phe Pro Asn Thr Arg Tyr Gly Ile Gly Cys Leu Ala Pro
        195                 200                 205

<210> SEQ ID NO 5
<211> LENGTH: 76
<212> TYPE: DNA
<213> ORGANISM: Artificial Sequence
<220> FEATURE:
<223> OTHER INFORMATION: Synthesized

<400> SEQUENCE: 5
gttttagagc tagaaatagc aagttaaaat aaggctagtc cgttatcaac ttgaaaaagt     60
ggcaccgagt cggtgc                                                    76

<210> SEQ ID NO 6
<211> LENGTH: 76
<212> TYPE: DNA
<213> ORGANISM: Artificial Sequence
<220> FEATURE:
<223> OTHER INFORMATION: Synthesized

<400> SEQUENCE: 6
guuuuagagc uagaaauagc aaguuaaaau aaggcuaguc cguuaucaac uugaaaaagu     60
ggcaccgagu cggugc                                                    76

<210> SEQ ID NO 7
<211> LENGTH: 1795
<212> TYPE: DNA
<213> ORGANISM: Artificial Sequence
<220> FEATURE:
<223> OTHER INFORMATION: Synthesized

<400> SEQUENCE: 7
agttcatcac taatcacact tattgtgccc tcgacgagta tctatagcta gctcattaat     60
cgattcgggg gtgtgttgtc gaaggcggca atggcgagct actcgtcgcg gcgtccatgc    120
aatacctgta gcacgaaggc gatggccggg agcgtggtcg gcgagcccgt cgtgctgggg    180
cagagggtga cggtgctgac ggtggacggc ggcggcgtcc ggggtctcat cccgggaacc    240

-continued

| | |
|---|---|
| atcctcgcct tcctggaggc caggctgcag gagctggacg gaccggaggc gaggctggcg | 300 |
| gactacttcg actacatcgc cggaaccagc accggcggtc tcatcaccgc catgctcacc | 360 |
| gcgcccggca aggacaagcg gcctctctac gctgccaagg acatcaacca cttttacatg | 420 |
| cagaactgcc cgcgcatctt tcctcagaag tgagtccgat gctgccgcca ttgttcttgc | 480 |
| atccatccag catcgtacgt acgtcctcta tacatctgcg gatcatcatg tgcgcatgtt | 540 |
| tgtggcatgc atgcatgcat gtgagcagga gcaggcttgc ggccgccatg tccgcgctga | 600 |
| ggaagccaaa gtacaacggc aagtgcatgc gcagcctgat taggagcatc ctcggcgaga | 660 |
| cgagggtaag cgagacgctg accaacgtca tcatccctgc cttcgacatc aggctgctgc | 720 |
| agcctatcat cttctctacc tacgacgtac gtacgtcgtc acgaatgatt catctgtacg | 780 |
| tcgtcgcatg cgaatggctg cctacgtacg ccgtgcgcta acatactcag ctctttccta | 840 |
| tctgctgcgc caatttgcag gccaagagca cgcctctgaa gaacgctctg ctctcggacg | 900 |
| tgtgcattgg cacgtccgcc gcgccgacct acctcccggc gcactacttc cagactgaag | 960 |
| acgccaacgg caaggagcgc gaatacaacc tcatcgacgg cggtgtggcg ccaacaacc | 1020 |
| cggtaactga ctagctaact ggaaaacgga cgcacagact ccatgtccat ggcggcccac | 1080 |
| aaggtcgatg ctaattgttg cttatgtatg tcgcccgatt gcacatgcgt agacgatggt | 1140 |
| tgcgatgacg cagatcacca aaagatgct tgccagcaag acaaggccg aggagctgta | 1200 |
| cccagtgaag ccgtcgaact gccgcaggtt cctggtgctg tccatcggga cggggtcgac | 1260 |
| gtccgagcag ggcctctaca cggcgcggca gtgctcccgg tggggtatct gccggtggct | 1320 |
| ccgcaacaac ggcatggccc ccatcatcga catcttcatg gcggccagct cggacctggt | 1380 |
| ggacatccac gtcgccgcga tgttccagtc gctccacagc gacggcgact acctgcgcat | 1440 |
| ccaggacaac tcgctccgtg gcgccgcggc caccgtggac gcggcgacgc cggagaacat | 1500 |
| gcggacgctc gtcgggatcg gggagcggat gctggcacag agggtgtcca gggtcaacgt | 1560 |
| ggagacaggg aggtacgaac cggtgactgg cgaaggaagc aatgccgatg ccctcggtgg | 1620 |
| gctcgctagg cagctctccg aggagaggag aacaaggctc gcgcgccgcg tctctgccat | 1680 |
| caacccaaga ggctctagat gtgcgtcgta cgatatctaa gacaagtggc tttactgtca | 1740 |
| gtcacatgct tgtaaataag tagactttat tttaataaaa cataaaaata tatat | 1795 |

<210> SEQ ID NO 8
<211> LENGTH: 23
<212> TYPE: DNA
<213> ORGANISM: Artificial Sequence
<220> FEATURE:
<223> OTHER INFORMATION: Synthesized

<400> SEQUENCE: 8
tgatagcctc tgaaatggga act                                          23

<210> SEQ ID NO 9
<211> LENGTH: 20
<212> TYPE: DNA
<213> ORGANISM: Artificial Sequence
<220> FEATURE:
<223> OTHER INFORMATION: Synthesized

<400> SEQUENCE: 9
atagatggtg gattgagacg                                              20

<210> SEQ ID NO 10

<211> LENGTH: 20
<212> TYPE: DNA
<213> ORGANISM: Artificial Sequence
<220> FEATURE:
<223> OTHER INFORMATION: Synthesized

<400> SEQUENCE: 10
atggatcgca gcaacgccgg                                              20

<210> SEQ ID NO 11
<211> LENGTH: 20
<212> TYPE: DNA
<213> ORGANISM: Artificial Sequence
<220> FEATURE:
<223> OTHER INFORMATION: Synthesized

<400> SEQUENCE: 11
ttacggagcc aaacaaccga                                              20

<210> SEQ ID NO 12
<211> LENGTH: 20
<212> TYPE: DNA
<213> ORGANISM: Artificial Sequence
<220> FEATURE:
<223> OTHER INFORMATION: Synthesized

<400> SEQUENCE: 12
cacgcccctc gccaccgcgc                                              20

<210> SEQ ID NO 13
<211> LENGTH: 20
<212> TYPE: DNA
<213> ORGANISM: Artificial Sequence
<220> FEATURE:
<223> OTHER INFORMATION: Synthesized

<400> SEQUENCE: 13
tggccaactt cctccccacg                                              20

<210> SEQ ID NO 14
<211> LENGTH: 21
<212> TYPE: DNA
<213> ORGANISM: Artificial Sequence
<220> FEATURE:
<223> OTHER INFORMATION: Synthesized

<400> SEQUENCE: 14
cgaaaacagt tccacgctct c                                            21

<210> SEQ ID NO 15
<211> LENGTH: 20
<212> TYPE: DNA
<213> ORGANISM: Artificial Sequence
<220> FEATURE:
<223> OTHER INFORMATION: Synthesized

<400> SEQUENCE: 15
catctcgaag gttagcagcg                                              20

<210> SEQ ID NO 16
<211> LENGTH: 52
<212> TYPE: DNA
<213> ORGANISM: Artificial Sequence
<220> FEATURE:
<223> OTHER INFORMATION: Synthesized

<400> SEQUENCE: 16
gcgccgcgcg gtggcgaggg gcgtgcctgg ccaacttcct ccccacgggc ac    52

<210> SEQ ID NO 17
<211> LENGTH: 30
<212> TYPE: DNA
<213> ORGANISM: Artificial Sequence
<220> FEATURE:
<223> OTHER INFORMATION: Synthesized

<400> SEQUENCE: 17
aggaagcgcc gcgcccgcac gggcacgctg    30

<210> SEQ ID NO 18
<211> LENGTH: 40
<212> TYPE: DNA
<213> ORGANISM: Artificial Sequence
<220> FEATURE:
<223> OTHER INFORMATION: Synthesized

<400> SEQUENCE: 18
gtccatgctg gccaacttca cgggcacgct gctaaccttc    40

<210> SEQ ID NO 19
<211> LENGTH: 40
<212> TYPE: DNA
<213> ORGANISM: Artificial Sequence
<220> FEATURE:
<223> OTHER INFORMATION: Synthesized

<400> SEQUENCE: 19
cgggaaggaa gcgccgcgcg cacgggcacg ctgctaacct    40

<210> SEQ ID NO 20
<211> LENGTH: 47
<212> TYPE: DNA
<213> ORGANISM: Artificial Sequence
<220> FEATURE:
<223> OTHER INFORMATION: Synthesized

<400> SEQUENCE: 20
gggcgcggga aggaagcgcc gcgcgtggcg aggggcgtgc agaagac    47

<210> SEQ ID NO 21
<211> LENGTH: 40
<212> TYPE: DNA
<213> ORGANISM: Artificial Sequence
<220> FEATURE:
<223> OTHER INFORMATION: Synthesized

<400> SEQUENCE: 21
cgggaaggaa gcgccgcgcg cacgggcacg ctgctaacct    40

<210> SEQ ID NO 22
<211> LENGTH: 40
<212> TYPE: DNA
<213> ORGANISM: Artificial Sequence
<220> FEATURE:
<223> OTHER INFORMATION: Synthesized

<400> SEQUENCE: 22
gtccatgctg gccaacttca cgggcacgct gctaaccttc    40

<210> SEQ ID NO 23
<211> LENGTH: 28
<212> TYPE: DNA

<213> ORGANISM: Artificial Sequence
<220> FEATURE:
<223> OTHER INFORMATION: Synthesized

<400> SEQUENCE: 23
tgcggtgtcc ggcgagggcc ccacgggc                                    28

<210> SEQ ID NO 24
<211> LENGTH: 41
<212> TYPE: DNA
<213> ORGANISM: Artificial Sequence
<220> FEATURE:
<223> OTHER INFORMATION: Synthesized

<400> SEQUENCE: 24
tcgaggtgcg cggcggcggg cgtgcagaag acgctctcca a                     41

<210> SEQ ID NO 25
<211> LENGTH: 40
<212> TYPE: DNA
<213> ORGANISM: Artificial Sequence
<220> FEATURE:
<223> OTHER INFORMATION: Synthesized

<400> SEQUENCE: 25
gtccatgctg gccaacttca cgggcacgct gctaaccttc                       40

<210> SEQ ID NO 26
<211> LENGTH: 41
<212> TYPE: DNA
<213> ORGANISM: Artificial Sequence
<220> FEATURE:
<223> OTHER INFORMATION: Synthesized

<400> SEQUENCE: 26
cggggaagga agcgccgcgc tcacgggcac gctgctaacc t                     41

<210> SEQ ID NO 27
<211> LENGTH: 37
<212> TYPE: DNA
<213> ORGANISM: Artificial Sequence
<220> FEATURE:
<223> OTHER INFORMATION: Synthesized

<400> SEQUENCE: 27
cccatggatc gcagcaacct tcgagatgct actcccg                          37

<210> SEQ ID NO 28
<211> LENGTH: 44
<212> TYPE: DNA
<213> ORGANISM: Artificial Sequence
<220> FEATURE:
<223> OTHER INFORMATION: Synthesized

<400> SEQUENCE: 28
agcgccgcgc ggtggcgagg ggcacgctgc taaccttcga gatg                  44

<210> SEQ ID NO 29
<211> LENGTH: 39
<212> TYPE: DNA
<213> ORGANISM: Artificial Sequence
<220> FEATURE:
<223> OTHER INFORMATION: Synthesized

<400> SEQUENCE: 29
cgggaaggaa gcgccgcgcc acgggcacgc tgctaacct                        39

<210> SEQ ID NO 30
<211> LENGTH: 34
<212> TYPE: DNA
<213> ORGANISM: Artificial Sequence
<220> FEATURE:
<223> OTHER INFORMATION: Synthesized

<400> SEQUENCE: 30
cgggaaggaa gcgccgcgct gcggaaaacg ctct                          34

<210> SEQ ID NO 31
<211> LENGTH: 30
<212> TYPE: DNA
<213> ORGANISM: Artificial Sequence
<220> FEATURE:
<223> OTHER INFORMATION: Synthesized

<400> SEQUENCE: 31
aggaagcgcc gcgcccgcac gggcacgctg                               30

<210> SEQ ID NO 32
<211> LENGTH: 40
<212> TYPE: DNA
<213> ORGANISM: Artificial Sequence
<220> FEATURE:
<223> OTHER INFORMATION: Synthesized

<400> SEQUENCE: 32
cgggaaggaa gcgccgcgcg cacgggcacg ctgctaacct                    40

<210> SEQ ID NO 33
<211> LENGTH: 47
<212> TYPE: DNA
<213> ORGANISM: Artificial Sequence
<220> FEATURE:
<223> OTHER INFORMATION: Synthesized

<400> SEQUENCE: 33
gggcgcggga aggaagcgcc gcgcgtggcg aggggcgtgc agaagac            47

<210> SEQ ID NO 34
<211> LENGTH: 41
<212> TYPE: DNA
<213> ORGANISM: Artificial Sequence
<220> FEATURE:
<223> OTHER INFORMATION: Synthesized

<400> SEQUENCE: 34
tcgaggtgcg cggcggcggg cgtgcagaag acgctctcca a                  41

<210> SEQ ID NO 35
<211> LENGTH: 40
<212> TYPE: DNA
<213> ORGANISM: Artificial Sequence
<220> FEATURE:
<223> OTHER INFORMATION: Synthesized

<400> SEQUENCE: 35
gtccatgctg gccaacttca cgggcacgct gctaaccttc                    40

<210> SEQ ID NO 36
<211> LENGTH: 41
<212> TYPE: DNA
<213> ORGANISM: Artificial Sequence
<220> FEATURE:

<223> OTHER INFORMATION: Synthesized

<400> SEQUENCE: 36
cggggaagga agcgccgcgc tcacgggcac gctgctaacc t                41

<210> SEQ ID NO 37
<211> LENGTH: 44
<212> TYPE: DNA
<213> ORGANISM: Artificial Sequence
<220> FEATURE:
<223> OTHER INFORMATION: Synthesized

<400> SEQUENCE: 37
agcgccgcgc ggtggcgagg ggcacgctgc taaccttcga gatg             44

<210> SEQ ID NO 38
<211> LENGTH: 85
<212> TYPE: DNA
<213> ORGANISM: Artificial Sequence
<220> FEATURE:
<223> OTHER INFORMATION: Synthesized

<400> SEQUENCE: 38
gagatgctac tccaagacgg gaggaagttc tccaaggtta gcatctccaa gacgtccatg    60
ctggccaacg tccatgctct ccaag                                         85

<210> SEQ ID NO 39
<211> LENGTH: 23
<212> TYPE: DNA
<213> ORGANISM: Artificial Sequence
<220> FEATURE:
<223> OTHER INFORMATION: Synthesized

<400> SEQUENCE: 39
cacaaactgg acaaagttga tgc                                    23

<210> SEQ ID NO 40
<211> LENGTH: 25
<212> TYPE: DNA
<213> ORGANISM: Artificial Sequence
<220> FEATURE:
<223> OTHER INFORMATION: Synthesized

<400> SEQUENCE: 40
tgacaacgct taaatgaacc ttgat                                  25

<210> SEQ ID NO 41
<211> LENGTH: 20
<212> TYPE: DNA
<213> ORGANISM: Artificial Sequence
<220> FEATURE:
<223> OTHER INFORMATION: Synthesized

<400> SEQUENCE: 41
acgtggagac agggaggtac                                        20

<210> SEQ ID NO 42
<211> LENGTH: 21
<212> TYPE: DNA
<213> ORGANISM: Artificial Sequence
<220> FEATURE:
<223> OTHER INFORMATION: Synthesized

<400> SEQUENCE: 42
gtacgacgca catctagagc c                                      21

```
<210> SEQ ID NO 43
<211> LENGTH: 20
<212> TYPE: DNA
<213> ORGANISM: Artificial Sequence
<220> FEATURE:
<223> OTHER INFORMATION: Synthesized

<400> SEQUENCE: 43
acgtggagac agggagcgag                                               20

<210> SEQ ID NO 44
<211> LENGTH: 20
<212> TYPE: DNA
<213> ORGANISM: Artificial Sequence
<220> FEATURE:
<223> OTHER INFORMATION: Synthesized

<400> SEQUENCE: 44
gcttctgggg ttgatggcag                                               20
```

MAIZE PARTHENOGENETIC HAPLOID-INDUCING GENE ZMPLA1E AND APPLICATION THEREOF

RELATED APPLICATIONS

The present application is a National Phase of International Application Number PCT/CN2018/121993, filed Dec. 19, 2018, and claims the priority of China Application No. 201810129251.8, filed Feb. 8, 2018.

INCORPORATION BY REFERENCE

The sequence listing provided in the file entitled SEQUENCE_LISTING_2020-11-05.txt, which is an ASCII text file that was created on Nov. 5, 2020, and which comprises 16,414 bytes, is hereby incorporated by reference in its entirety.

TECHNICAL FIELD

The present invention relates to the field of biotechnology, specifically relates to the maize parthenogenetic haploid-inducing gene ZmPLA1E and the application thereof, in particular to the maize parthenogenetic haploid-inducing gene ZmPLA1E and its application in producing and significantly enhancing the parthenogenetic haploid induction ability.

BACKGROUND ART

Maize is the largest crop in China, and in 2012, the maize planting area exceeded 34 million hm². Hybrid maize is used in more than 97% of the maize planting area in China (Li J, 2009). Breeding of excellent maize inbred lines is the basis and key for maize to use heterosis and breeding excellent hybrids. However, traditional breeding methods require 7-8 generations to obtain a relatively stable inbred line, while haploid breeding techniques require only 2 generations (Weber D F, 2014). Therefore, as a method to quickly obtain pure lines, haploid breeding techniques have been applied in large scale by many seed companies at home and abroad and has become one of the three core technologies for modern maize breeding comparable to transgenic technology and molecular marker-assisted breeding technology (Chen Shaojiang et al., 2009).

Since the method of producing a parthenogenetic haploid using a inducing-line by producing parthenogenesis has broad application prospects and value, thus a number of research institutes around the world have conducted extensive research on the genetic basis and biological basis of Stock6 and its derived lines to induce parthenogenetic haploids. The results showed that the trait of maize parthenogenesis induction producing maize haploid is heritable and is controlled by multiple genetic loci. Röber et al. (1999) detected two genetic loci controlling the induction rate trait for the first time, which were located on chromosome 1 and chromosome 2, respectively, and explained about 17.9% of phenotypic variation. Barrant et al. (2008) also detected a major QTL affecting the haploid induction rate and causing the population segregation distortion in the same region of chromosome 1. Prigge et al. (2012) used multiple populations for genome-wide scanning and found eight genetic loci controlling the induction rate, of which two were QTLs. The major QTL locus qhir1 in the 1.04bin region on chromosome 1 can explained 66% of the genetic variation, and the major QTL locus qhir8 in the 9.01bin region on chromosome 9 can explained 20% of the genetic variation. Among them, qhir1 has been mapped to the 243 kb physical interval (Dong X et al., 2013), and a phospholipase gene was successfully cloned in this region and the loss of function of this gene can induce haploid production (Kelliher T et al., 2017; Liu C et al, 2017; Gilles L M, et al, 2017). As another major QTL, qhir8 can significantly increase haploid induction rate. Liu et al. (2015) fine-mapped qhir8 using the hybrid progeny of the inducing line CAUHOI (2%) with a low induction ability and the inducing line UH400 (8%) with a high induction rate as the mapping population, and finally qhir8 was mapped between the marker 4292232 and marker umc1867, and the physical distance was about 789kb.

SUMMARY OF THE INVENTION

One object of the present invention is to provide a method for preparing a plant maternal haploid-inducing line.

The method for preparing a plant maternal haploid-inducing line provided by the present invention comprises the following steps: silencing or inhibiting the expression and/or activity of the ZmPLA1E gene in the genome of a target plant or knocking out the ZmPLA1E gene to obtain a transgenic plant, i.e., the plant maternal haploid-inducing line.

In the above method, the silencing or inhibiting the expression and/or activity of the ZmPLA1E gene in the genome of the target plant or knocking out the ZmPLA1E gene is mutating the ZmPLA1E gene in the genome of the target plant to reduce the expression level of the ZmPLA1E gene in the genome of the target plant or cause a deletion mutation, insertion mutation or base substitution of the ZmPLA1E gene in the genome of the target plant.

In the above methods, the method of reducing the expression level of the ZmPLA1E gene in the genome of the target plant can be RNAi interference or overexpression or promoter editing. The RNAi interference can be single-stranded RNA interference, such as miRNA, or double-stranded RNA interference, such as siRNA, dsRNA, shRNA, and the like.

The method of causing a deletion mutation, insertion mutation or base substitution of the ZmPLA1E gene in the genome of the target plant can be CRISPR/Cas9, TELLEN, T-DNA insertion or EMS mutagenesis.

Further, the method of causing a deletion mutation, insertion mutation or base substitution of the ZmPLA1E gene in the genome of the target plant can be CRISPR/Cas9.

Still further, the target sequence of the CRISPR/Cas9 is positions 163-182 or 210-229 of SEQ ID NO: 1; the sgRNA sequence of the CRISPR/Cas9 is SEQ ID NO: 6.

In a specific embodiment of the present invention, the method of causing a deletion mutation, insertion mutation or base substitution of the ZmPLA1E gene in the genome of the target plant comprises the following steps: introducing a CRISPR/Cas9 vector expressing the sgRNA into a target plant, to obtain a transgenic plant. The CRISPR/Cas9 vector is specifically a vector obtained by inserting the encoding DNA molecule of the sgRNA set forth in SEQ ID NO: 5 into the pBUE411 vector.

Another object of the present invention is to provide a method for preparing a plant maternal haploid.

The method for preparing a plant maternal haploid provided by the present invention comprises the following steps: self-crossing the plant maternal haploid-inducing line prepared by the above method or a progeny thereof or hybridizing it as a male parent with other plant materials, to obtain a self-crossed progeny or hybrid progeny, i.e., the plant maternal haploid.

The method for preparing the plant maternal haploid further comprises the following steps: conducting haploid trait identification, leaf ploidy identification and/or molecular marker identification on the self-crossed progeny or hybrid progeny, and selecting one of the progeny identified as a haploid by at least one method to be the plant maternal haploid.

The haploid trait identification method can be carried out according to the following method: if the plant to be tested has the characteristics of short plant, narrow and upswept leaves, compact plant type, male sterility, etc., the plant is a haploid or a candidate haploid; if the plant to be tested has the characteristics of tall plant, wide leaves, scatter, normal fertility, etc., the plant is a diploid or a candidate diploid.

The leaf ploidy identification method can be carried out according to the following method: extracting the cell nuclei of the young leaves of the plant to be tested, using diploid maize leaves as a control; and detecting the signal by flow cytometry, first detecting the diploid cell nuclei signal, and setting the diploid cell nuclei signal peak to 100 (since the genetic material in the diploid cells is twice the genetic material in the haploid cells, the haploid cell nuclei signal peak appears near 50). If the cell nuclei signal peak of the plant to be tested appears near 50, the plant is a haploid or a candidate haploid; if the signal peak of the plant to be tested appears near 100, which is the same as the diploid cell nuclei signal intensity enrichment position, the plant is a diploid or a candidate diploid.

The molecular marker identification can be carried out according to the following method: using polymorphic primers between the male parent (maternal haploid-inducing line) and the female parent to conduct PCR amplification, and determining the plant to be tested is a haploid or a diploid according to the PCR amplification product: if the amplification product of the plant to be tested only has the band type of the female parent and no band type of the male parent, the plant is a haploid or a candidate haploid; if the amplification product of the plant to be tested has a heterozygous band type of the male parent and the female parent, the plant is a diploid or a candidate diploid.

Both the plant maternal haploid-inducing line and the plant maternal haploid prepared by the above methods are within the protection scope of the present invention.

Still another object of the present invention is to provide a protein.

The protein provided by the present invention is a protein of the following a) or b) or c) or d):
a) a protein with the amino acid sequence set forth in SEQ ID NO: 3 or SEQ ID NO: 4;
b) a fusion protein obtained by attaching tag(s) to the N-terminus or/and C-terminus of the protein set forth in SEQ ID NO: 3 or SEQ ID NO: 4;
c) a protein having the same function and obtained by subjecting the amino acid sequence set forth in SEQ ID NO: 3 or SEQ ID NO: 4 to substitution and/or deletion and/or addition of one or more amino acid residues;
d) a protein having 75% or more of homology with the amino acid sequence set forth in SEQ ID NO: 3 or SEQ ID NO: 4 and having the same function.

The amino acid sequence of the protein encoded by the haploid-inducing gene ZmPLA1E of the present invention is set forth in SEQ ID NO: 3. The amino acid sequence of the protein encoded by the mutated ZmPLA1E can be set forth in SEQ ID NO: 4, such as the amino acid sequence of the ZmPLA1E protein in CAU5. The amino acid sequence of the ZmPLA1E protein set forth in SEQ ID NO: 3 and the amino acid sequence (such as, set forth in SEQ ID NO: 4) obtained by modifying the ZmPLA1E protein set forth in SEQ ID NO: 3 to lose function are both within the protection scope of the present invention.

Still another object of the present invention is to provide a biological material related to the above protein.

The biological material related to the above protein provided by the present invention is any one of the following A1) to A12):
A1) a nucleic acid molecule encoding the above protein;
A2) an expression cassette containing the nucleic acid molecule of A1);
A3) a recombinant vector containing the nucleic acid molecule of A1);
A4) a recombinant vector containing the expression cassette of A2);
A5) a recombinant microorganism containing the nucleic acid molecule of A1);
A6) a recombinant microorganism containing the expression cassette of A2);
A7) a recombinant microorganism containing the recombinant vector of A3);
A8) a recombinant microorganism containing the recombinant vector of A4);
A9) a transgenic plant cell line containing the nucleic acid molecule of A1);
A10) a transgenic plant cell line containing the expression cassette of A2);
A11) a transgenic plant cell line containing the recombinant vector of A3);
A12) a transgenic plant cell line containing the recombinant vector of A4).

In the above related biological material, the nucleic acid molecule of A1) is a gene represented by the following 1) or 2) or 3):
1) a cDNA molecule or genomic DNA molecule whose encoding sequence is set forth in SEQ ID NO: 1 or SEQ ID NO: 2;
2) a cDNA molecule or genomic DNA molecule having 75% or more identity with the nucleotide sequence defined in 1) and encoding the above protein;
3) a cDNA molecule or genomic DNA molecule that can hybridize to the nucleotide sequence defined in 1) or 2) under stringent conditions and encode the above protein.

The sequence of the haploid-inducing gene ZmPLA1E of the present invention is set forth in SEQ ID NO: 1. The sequence of the mutated ZmPLA1E gene can be SEQ ID NO: 2, such as the sequence of the ZmPLA1E gene in CAU5. The sequence of the ZmPLA1E gene set forth in SEQ ID NO: 1 and the DNA molecule obtained by modifying the sequence of the ZmPLA1E gene set forth in SEQ ID NO: 1 by a deletion mutation, insertion mutation or base substitution are both within the protection scope of the present invention.

A final object of the present invention is to provide any one of the following 1)-6) uses
1) use of a plant maternal haploid-inducing line prepared by the above method in the preparation of a plant maternal haploid;
2) use of a substance silencing or inhibiting the expression and/or activity of the ZmPLA1E gene in the genome of the target plant or knocking out the ZmPLA1E gene in the preparation of a plant maternal haploid-inducing line or a plant maternal haploid;

3) use of a plant maternal haploid-inducing line prepared by the above method or a plant maternal haploid prepared by the above method in plant hybrid breeding or plant haploid breeding;
4) use of the above protein or the biological material for regulating the induction rate of a plant maternal haploid-inducing line;
5) use of the above protein or the biological material for increasing the induction rate of a plant maternal haploid-inducing line;
6) use of the above protein or the biological material for cultivating a plant maternal haploid.

In the above use, the substance that knocks out the ZmPLA1E gene is the above CRISPR/Cas9 vector expressing the sgRNA. The CRISPR/Cas9 vector is specifically a vector obtained by inserting the encoding DNA molecule of the sgRNA set forth in SEQ ID NO: 5 into the pBUE411 vector.

In the above uses or methods, the target plant or plant can be maize; the maize can be wild-type maize B104.

DETAILED DESCRIPTION OF THE INVENTION

The experimental methods used in the following examples are conventional methods unless otherwise specified.

The materials, reagents and the like used in the following examples are commercially available unless otherwise specified.

The pBUE411 vector in the following examples is described in the literature "A CRISPR/Cas9 toolkit for multiplexing genome editing in plants. Xing H L, Dong L, Wang Z P, Zhang H Y, Han C Y, Liu B, Wang X C, Chen Q J. BMC Plant Biol. 2014 Nov. 29; 14(1): 327.10.1186/s12870-014-0327-y PubMed 25432517". This biomaterial is available to the public from the author of the article and is used only for repeating the related experiments of the present invention and cannot be used for other purposes.

The CAU5 in the following examples is described in the literature "Dong, X., et al. (2014). "Marker-assisted selection and evaluation of high oil in vivo haploid inducers in maize." Molecular Breeding 34(3): 1147-1158". This biomaterial is available to the public from the applicant and is used only for repeating the related experiments of the present invention and cannot be used for other purposes.

The CAUHOI in the following examples is described in the literature "Li, L. and X. Xu, et al. (2009). "Morphological and molecular evidences for DNA introgression in haploid induction via a high oil inducer CAUHOI in maize." Planta 230 (2): 367-376". This biomaterial is available to the public from the applicant and is used only for repeating the related experiments of the present invention and cannot be used for other purposes.

The wild-type maize B104 in the following examples is described in the literature "Hallauer A R, Lamkey K R, White P R. Registration of five inbred lines of maize: B102, B103, B104, B105, and B106 [J]. Crop science, 1997, 37(4): 1405-1406". This biomaterial is available to the public from the applicant and is used only for repeating the related experiments of the present invention and cannot be used for other purposes.

Example 1. Cloning of Maize Parthenogenetic Haploid-Inducing Gene ZmPLA1E

1) Preliminary Mapping of Maize Parthenogenetic Haploid-Inducing Gene ZmPLA1E

Figure 1:
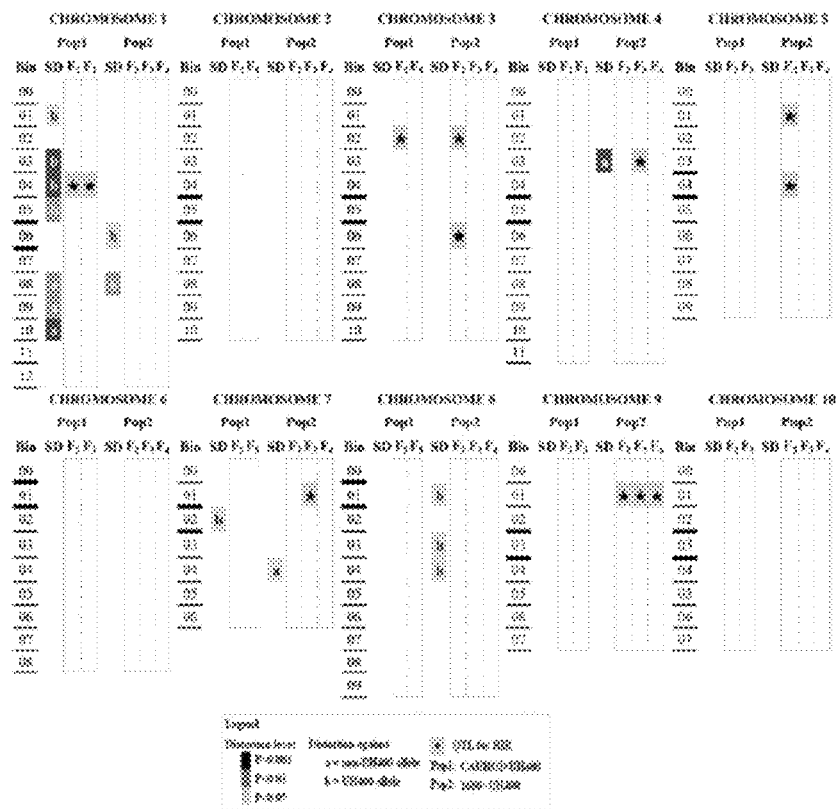
FIG. 1 shows the preliminary mapping results.

In order to isolate the ZmPLA1E gene, the present invention employed the map-based cloning method to first establish a large mapping population with high polymorphism, consisting of the hybrid progeny of the inducing line CAUHOI (2%) with a low induction ability and the inducing line UH400 (8%) with a high induction rate. The polymorphic molecular markers of the two parents were used to conduct the preliminary mapping of the maize parthenogenetic haploid-inducing gene. The preliminary mapping results are shown in FIG. 1. The mapping results indicated that the haploid-inducing gene ZmPLA1E was preliminarily mapped at 9.01 bin of chromosome 9, between the two markers bnlg1272 and umc1040.

2) Fine Mapping of Maize Parthenogenetic Haploid-Inducing Gene ZmPLA1E

Figure 2:
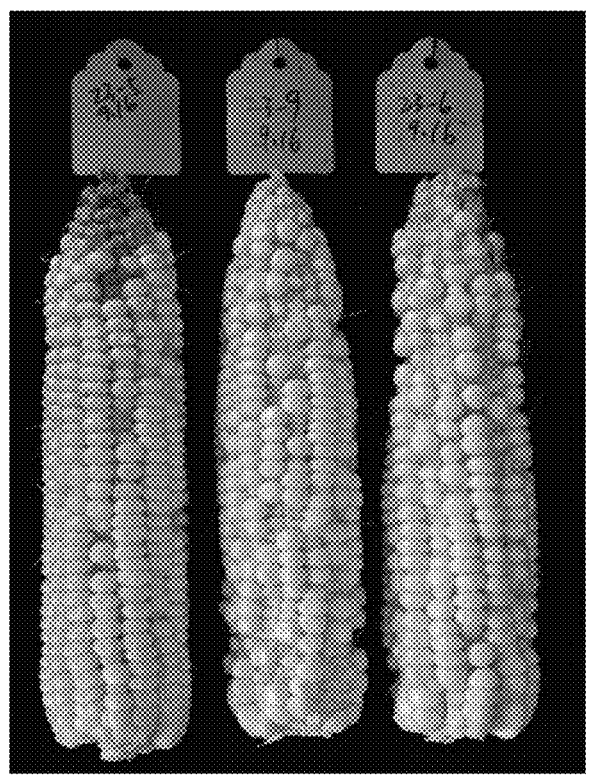
FIG. 2 shows the phenotypes of the families of the exchanged individuals. Left: the ZmPLA1E gene has no mutation; middle: the ZmPLA1E gene has a heterozygous mutation; right: the ZmPLA1E gene has a homozygous mutation.
Figure 3:
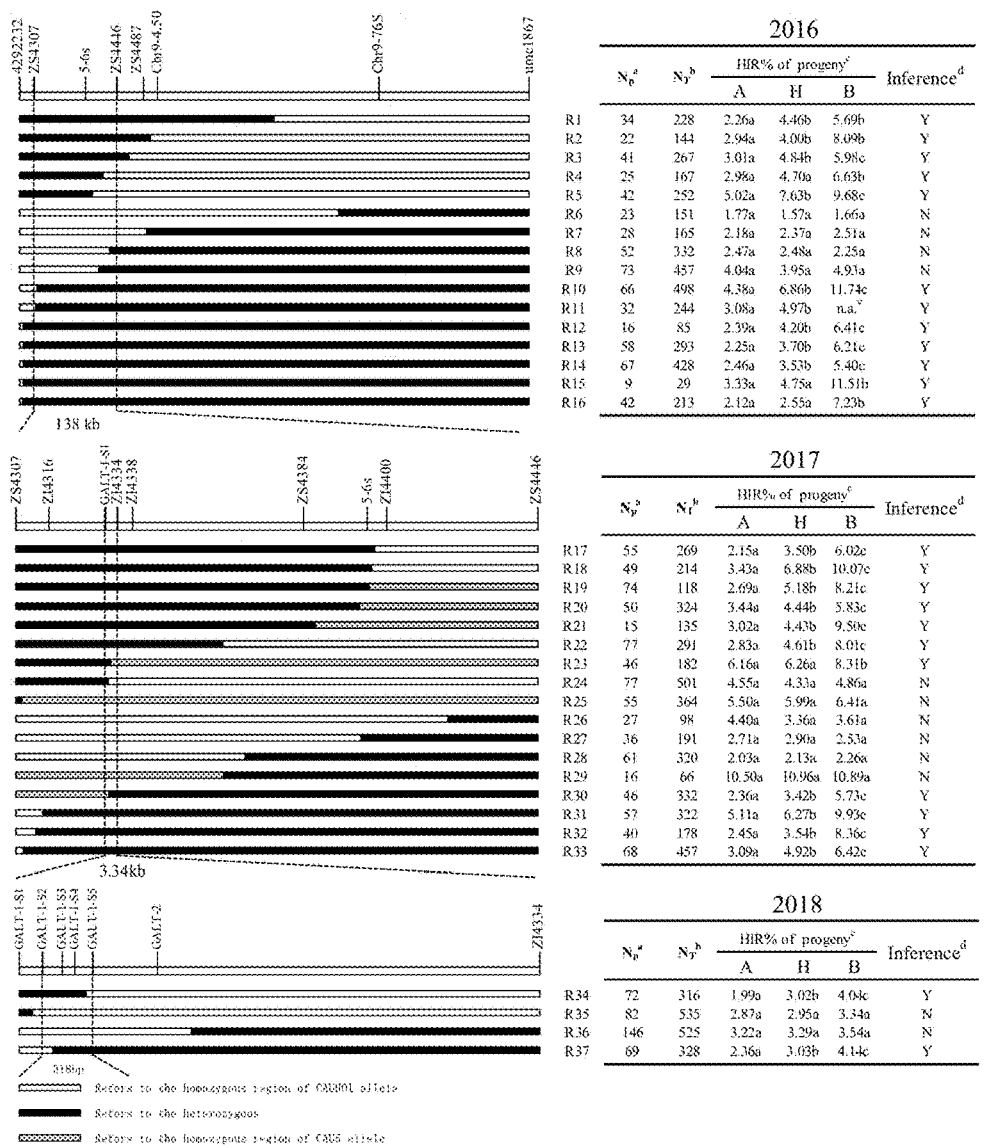
FIG. 3 shows the fine mapping results.

The F2 large population was assembled from the inducing line CAUHOI (2%) with a low induction ability and the inducing line CAU5 (8%) or UH400 (8%) with a high induction rate, and these individual plants were detected by molecular markers bnlg1272 and umc1040. The newly developed molecular markers covering the region between the molecule markers bnlg1272 and umc1040 was used to detect and screen the exchanged individual plants from the large population and the exact exchange positions of the exchanged individual plants were determined by these high-density molecular markers. The families of the self-crossed plants of these exchanged individual plants were further planted in the field, and their genotypes and induction rates were tested, and the gene was mapped by combining the genotypes and induction rates of each family of the exchanged individual plants. The phenotypes of the families of the exchanged individual plants are shown in FIG. 2. The fine mapping results are shown in FIG. 3. The fine mapping results indicated that the haploid-inducing gene ZmPLA1E was finally mapped between the two markers GALT-1S2 and GALT-1S5, and its physical distance to B73 was 318 bp. By viewing the B73 sequence of 318 bp, it was found that it only covered one predicted gene, and the present invention named this candidate gene ZmPLA1E.

3) Screening and Sequencing of BAC Library of CAU5

In order to obtain the CAU5 sequence within the candidate interval range and more sequence information of its two sides, the BAC library of the CAU5 was screened by molecular markers near the mapped interval, and finally 4 positive monoclonals were screened. By comparison, the monoclonal A52 with the longest inserted fragment was selected for sequencing.

4) Sequence Alignment of ZmPLA1E Alleles in CAUHOI and CAU5

Since there is no BAC library of the CAUHOI, in order to obtain the DNA sequence of the candidate gene ZmPLA1E in the CAUHOI and analyze the difference in DNA level between the ZmPLA1E alleles in the CAUHOI and CAU5, the present invention utilized the primers ZmPLA1E-FL-F/ZmPLA1E-FL-R to conduct the PCR amplification and sequencing of the allele ZmPLA1E in the CAUHOI.

The sequences of the primers for the PCR amplification of the allele ZmPLA1E in the CAUHOI are as follows:

```
ZmPLA1E-FL-F:
                                    (SEQ ID NO: 8)
TGATAGCCTCTGAAATGGGAACT;

ZmPLA1E-FL-R:
                                    (SEQ ID NO: 9)
ATAGATGGTGGATTGAGACG.
```

After obtaining the sequence of the allele ZmPLA1E in the CAUHOI, the polymorphism of the ZmPLA1E alleles between the CAUHOI and CAU5 was analyzed. It was found that the allele ZmPLA1E has 6 SNP polymorphism sites between the CAUHOI and CAU5, and 4 of them can lead to amino acid substitution mutation.

5) Full-Length cDNA Clone of ZmPLA1E Allele in CAUHOI and CAU5

In order to further confirm whether the difference between the ZmPLA1E alleles in the CAUHOI and CAU5 would change its transcript, the present invention cloned the full length cDNA of the ZmPLA1E alleles in the CAUHOI and CAU5, respectively. The specific method was as follows:

5-1) Primer design: primers were designed according to the transcript provided by the B73 reference sequence; primer sequences are as follows:

```
F:
                                    (SEQ ID NO: 10)
ATGGATCGCAGCAACGCCGG;

R:
                                    (SEQ ID NO: 11)
TTACGGAGCCAAACAACCGA.
```

5-2) Extraction of total RNA: total RNA was extracted from seeds of the CAUHOI and CAU5 five days after pollination using the RNAprep Pure Plant Kit (DP441) from TIANGEN.

5-3) Acquisition of cDNA: the extracted total RNA was reverse transcribed using the TransScript One-Step gDNA Removal and cDNA Synthesis SuperMix from the TransGen to obtain cDNA.

5-4) The obtained cDNA was amplified as a template to obtain a PCR product, and the PCR product was ligated to a T vector, and a positive monoclonal was selected for sequencing.

The sequencing results showed that an amplification product of 1061 bp was obtained by PCR amplification in the CAUHOI and its nucleotide sequence was set forth in SEQ ID NO: 1. The gene set forth in SEQ ID NO: 1 was named ZmPLA1E gene. The open reading frame (ORF) is positions 78-695 of SEQ ID NO: 1 and the ZmPLA1E gene encodes the protein set forth in SEQ ID NO: 3. The amino acid sequence set forth in SEQ ID NO: 3 was named ZmPLA1E protein.

An amplification product of 1055 bp was obtained by PCR amplification in the CAU5 and its nucleotide sequence was set forth in SEQ ID NO: 2. The gene set forth in SEQ ID NO: 2 was named the mutant ZmPLA1E gene. The open reading frame (ORF) is positions 78-695 of SEQ ID NO: 2 and the mutant ZmPLA1E gene encodes the protein set forth in SEQ ID NO: 4. The amino acid sequence set forth in SEQ ID NO: 4 was named mutant ZmPLA1E protein.

After comparison, it was found that in the CAU5, the ZmPLA1E allele was mutated in four SNPs, resulting in amino acid substitution: M44T, A87T, T153A and G183A. It was predicted that these four SNPs were located on the four transmembrane domains of the protein, and these mutations would change its transmembrane structure and then affect its function.

Example 2. Application of Maize Parthenogenetic Haploid-Inducing Gene ZmPLA1E in Producing and Significantly Enhancing Parthenogenetic Haploid Induction Ability I. Knockout of Maize ZmPLA1E Gene Using CRISPR/Cas9 System.

The maize ZmPLA1E gene was knocked out using the CRISPR/Cas9 system to obtain a transgenic maize ZmPLA1E gene mutant. The Specific steps were as follows:

1) Selection of sgRNA Sequence

The target site sequences were designed on the maize ZmPLA1E gene and the length was 20 bp.

Target site 1 is located at positions 163-182 of SEQ ID NO: 1, and the sequence of the target site 1 is CACGCCCCTCGCCACCGCGC (SEQ ID NO: 12).

Target site 2 is located at positions 210-229 of SEQ ID NO: 1, and the sequence of the target site 2 is TGGCCAACTTCCTCCCCACG (SEQ ID NO: 13).

The sgRNA sequence for the designed target sites is GUUUUAGAGCUA-GAAAUAGCAAGUUAAAAUAAGGCUAGU-CCGUUAUCAACU UGAAAAAGUGGCACCGAGUCG-GUGC (SEQ ID NO: 6), and the encoding DNA molecule of the sgRNA is set forth in SEQ ID NO: 5.

2) Construction of CRISPR/Cas9 Vector

The CRISPR/Cas9 vector is a vector obtained by inserting the encoding DNA molecule of the sgRNA set forth in SEQ ID NO: 5 in the sequence listing into the pBUE411 vector.

3) Acquisition of Transgenic Maize

The CRISPR/Cas9 vector obtained in step 2) was transformed into *Agrobacterium* competent cell EHA105 by heat shock (*Agrobacterium* EHA105 competent cell was purchased from OCEANTOPS, and is commercially available to the public) to obtain the recombinant bacteria EHA105/CRISPR/Cas9.

The recombinant bacteria EHA105/CRISPR/Cas9 was transformed into maize B104 (National Maize Improvement Center, China Agricultural University) young embryos through *Agrobacterium* infection method (the recombinant *Agrobacterium* was subjected to propagation at 28° C., and the bacteria liquid after propagation was used to infect the maize young embryos) and after screening, differentiation and rooting, T0 generation transgenic maize plants were obtained.

4) Identification of Transgenic Maize with Mutant ZmPLA1E Gene

The leaves of the T0 generation transgenic maize plants obtained in step 3) were collected, and the genomic DNA was extracted and used as a template, and PCR amplification was carried out using the following primers to obtain PCR amplification products of different strains.

The sequences of the primers for detecting the mutant ZmPLA1E sequence are as follows:

```
ZmPLA1E_F:
                                        (SEQ ID NO: 14)
CGAAAACAGTTCCACGCTCTC;

ZmPLA1E_R:
                                        (SEQ ID NO: 15)
CATCTCGAAGGTTAGCAGCG.
```

The PCR amplification products of different strains were subjected to Sanger sequencing, and aligned with the ZmPLA1E gene in wild-type maize B104 according to the sequencing results.

If a strain has a sequence with bimodal characteristics from the target site sequence, its genotype is a heterozygous genotype (the ZmPLA1E gene is mutated on one of two homologous chromosomes, and the ZmPLA1E is not mutated on the other chromosome), and the strain is a strain of T0 generation transgenic maize with a heterozygous mutation in ZmPLA1E gene;

If a strain has a sequence with a specific unimodal characteristics from the target site sequence, and has the same sequence as the ZmPLA1E gene sequence of wild-type maize B104, its genotype is wild-type, i.e., the ZmPLA1E gene sequence is not mutated, the following analysis can be ignored; if there is a mutation, its genotype is a homozygous genotype (the ZmPLA1E gene is mutated on the two homologous chromosomes), and the strain is a strain of T0 generation transgenic maize with a homozygous mutation in ZmPLA1E gene.

The identification results are shown in Tables 1 and 2 (Table 1 shows the mutations of the allele 1 (i.e., the ZmPLA1E gene in one homologous chromosome) of the T0 generation transgenic maize plants; Table 2 shows the mutations of the allele 2 (i.e., the ZmPLA1E gene in the other homologous chromosome) of the T0 generation transgenic maize plant): among the 24 T0 generation transgenic maize plants, the ZmPLA1E gene of 14 T0 generation transgenic maize plants was mutated, wherein 7 plants had a homozygous mutation in ZmPLA1E gene. Further, the individual plants causing the shift mutation (the deletion is not a multiple of 3) in the homozygous mutant individual plants were selected for phenotype identification, and the specific individual plant numbers were as follows: T0-8, T0-13, T0-15 and T0-17.

TABLE 1

Allele 1 sequence

| T0 ID | Mutation type | Allele 1 sequence (mutation) |
|---|---|---|
| WT | wild-type | GCGCCGCGCGGTGGCGAGGGGCGTGC(26 bp)CTGGCCAACTTCCTCCCCACGGGCAC (SEQ ID NO: 16) |
| T0-1 | wild-type | GCGCCGCGCGGTGGCGAGGGGCGTGC(26 bp)CTGGCCAACTTCCTCCCCACGGGCAC(wild-type) (SEQ ID NO: 16) |
| T0-2 | wild-type | GCGCCGCGCGGTGGCGAGGGGCGTGC(26 bp)CTGGCCAACTTCCTCCCCACGGGCAC(wild-type) (SEQ ID NO: 16) |
| T0-3 | wild-type | GCGCCGCGCGGTGGCGAGGGGCGTGC(26 bp)CTGGCCAACTTCCTCCCCACGGGCAC(wild-type) (SEQ ID NO: 16) |
| T0-4 | wild-type | GCGCCGCGCGGTGGCGAGGGGCGTGC(26 bp)CTGGCCAACTTCCTCCCCACGGGCAC(wild-type) (SEQ ID NO: 16) |
| T0-5 | homozygous | AGGAAGCGCCGCGC(-57 bp)CCGCACGGGCACGCTG(deletion) (SEQ ID NO: 17) |
| T0-6 | heterozygous | GTCCATGCTGGCCAACTTC(-6 bp;+85 bp)ACGGGCACGCTGCTAACCTTC(deletion and insertion) (SEQ ID NO: 18) |
| T0-7 | wild-type | GCGCCGCGCGGTGGCGAGGGGCGTGC(26 bp)CTGGCCAACTTCCTCCCCACGGGCAC(wild-type) (SEQ ID NO: 16) |
| T0-8 | homozygous | CGGGAAGGAAGCGCCGCGCG(-59 bp)CACGGGCACGCTGCTAACCT(deletion) (SEQ ID NO: 19) |
| T0-9 | homozygous | GGGCGCGGGAAGGAAGCGCCGCGCG(-1 bp)TGGCGAGGGGCGTGCAGAAGAC(deletion) (SEQ ID NO: 20) |
| T0-10 | heterozygous | CGGGAAGGAAGCGCCGCGCG(-59 bp)CACGGGCACGCTGCTAACCT(deletion) (SEQ ID NO: 21) |
| T0-11 | heterozygous | GTCCATGCTGGCCAACTTC(-6 bp;+85 bp)ACGGGCACGCTGCTAACCTTC(deletion and insertion) (SEQ ID NO: 22) |

TABLE 1-continued

Allele 1 sequence

| T0 ID | Mutation type | Allele 1 sequence (mutation) |
|---|---|---|
| T0-12 | heterozygous | TGCGGTGTCCGGCGAG(-62 bp)GG(30 bp)CCC(+1 bp)CACGGGC(deletion and insertion) (SEQ ID NO: 23) |
| T0-13 | homozygous | TCGAGGTGCGCGGCGGCG(-50 bp)GGCGTGCAGAAGACGCTCTCCAA(deletion) (SEQ ID NO: 24) |
| T0-14 | wild-type | GCGCCGCGCGGTGGCGAGGGGCGTGC(26 bp)CTGGCCAACTTCCTCCCCACGGGCAC(wild-type) (SEQ ID NO: 16) |
| T0-15 | homozygous | GTCCATGCTGGCCAACTTC(-6 bp;+85 bp)ACGGGCACGCTGCTAACCTTC(deletion and insertion) (SEQ ID NO: 25) |
| T0-16 | wild-type | GCGCCGCGCGGTGGCGAGGGGCGTGC(26 bp)CTGGCCAACTTCCTCCCCACGGGCAC(wild-type) (SEQ ID NO: 16) |
| T0-17 | homozygous | CGGGGAAGGAAGCGCCGCGCT(-59 bp)CACGGGCACGCTGCTAACCT(substitution and deletion) (SEQ ID NO: 26) |
| T0-18 | heterozygous | CCCATGGATCGCAGCAAC(-152 bp)CTTCGAGATGCTACTCCCG(deletion) (SEQ ID NO: 27) |
| T0-19 | wild-type | GCGCCGCGCGGTGGCGAGGGGCGTGC(26 bp)CTGGCCAACTTCCTCCCCACGGGCAC(wild-type) (SEQ ID NO: 16) |
| T0-20 | homozygous | AGCGCCGCGCGGTGGCGAGGG(-54 bp)GCACGCTGCTAACCTTCGAGATG(deletion) (SEQ ID NO: 28) |
| T0-21 | wild-type | GCGCCGCGCGGTGGCGAGGGGCGTGC(26 bp)CTGGCCAACTTCCTCCCCACGGGCAC(wild-type) (SEQ ID NO: 16) |
| T0-22 | wild-type | GCGCCGCGCGGTGGCGAGGGGCGTGC(26 bp)CTGGCCAACTTCCTCCCCACGGGCAC(wild-type) (SEQ ID NO: 16) |
| T0-23 | heterozygous | CGGGAAGGAAGCGCCGCGC(-60 bp;+382 bp)CACGGGCACGCTGCTAACCT(deletion and insertion) (SEQ ID NO: 29) |
| T0-24 | heterozygous | CGGGAAGGAAGCGCCGCGCTGCGGAAA--------------ACGCTCT(substitution and deletion) (SEQ ID NO: 30) |

TABLE 2

Allele 2 gene sequence

| T0 ID | Mutation type | Allele 2 sequence (mutation) |
|---|---|---|
| WT | wild-type | GCGCCGCGCGGTGGCGAGGGGCGTGC(26 bp)CTGGCCAACTTCCTCCCCACGGGCAC (SEQ ID NO: 16) |
| T0-1 | wild-type | GCGCCGCGCGGTGGCGAGGGGCGTGC(26 bp)CTGGCCAACTTCCTCCCCACGGGCAC(wild-type) (SEQ ID NO: 16) |
| T0-2 | wild-type | GCGCCGCGCGGTGGCGAGGGGCGTGC(26 bp)CTGGCCAACTTCCTCCCCACGGGCAC(wild-type) (SEQ ID NO: 16) |
| T0-3 | wild-type | GCGCCGCGCGGTGGCGAGGGGCGTGC(26 bp)CTGGCCAACTTCCTCCCCACGGGCAC(wild-type) (SEQ ID NO: 16) |
| T0-4 | wild-type | GCGCCGCGCGGTGGCGAGGGGCGTGC(26 bp)CTGGCCAACTTCCTCCCCACGGGCAC(wild-type) (SEQ ID NO: 16) |
| T0-5 | homozygous | AGGAAGCGCCGCGC(-57 bp)CCGCACGGGCACGCTG(deletion) (SEQ ID NO: 31) |
| T0-6 | heterozygous | GCGCCGCGCGGTGGCGAGGGGCGTGC(26 bp)CTGGCCAACTTCCTCCCCACGGGCAC(wild-type) (SEQ ID NO: 16) |

TABLE 2-continued

| | | Allele 2 gene sequence |
|---|---|---|
| T0 ID | Mutation type | Allele 2 sequence (mutation) |
| T0-7 | wild-type | GCGCCGCGCGGTGGCGAGGGGCGTGC(26 bp)CTGGCCAACTTCCTCCCCACGGGCAC(wild-type)<br>(SEQ ID NO: 16) |
| T0-8 | homozygous | CGGGAAGGAAGCGCCGCGCG(-59 bp)CACGGGCACGCTGCTAACCT(deletion)<br>(SEQ ID NO: 32) |
| T0-9 | homozygous | GGGCGCGGGAAGGAAGCGCCGCGCG(-1 bp)TGGCGAGGGGCGTGCAGAAGAC(deletion)<br>(SEQ ID NO: 33) |
| T0-10 | heterozygous | GCGCCGCGCGGTGGCGAGGGGCGTGC(26 bp)CTGGCCAACTTCCTCCCCACGGGCAC(wild-type)<br>(SEQ ID NO: 16) |
| T0-11 | heterozygous | GCGCCGCGCGGTGGCGAGGGGCGTGC(26 bp)CTGGCCAACTTCCTCCCCACGGGCAC(wild-type)<br>(SEQ ID NO: 16) |
| T0-12 | heterozygous | GCGCCGCGCGGTGGCGAGGGGCGTGC(26 bp)CTGGCCAACTTCCTCCCCACGGGCAC(wild-type)<br>(SEQ ID NO: 16) |
| T0-13 | homozygous | TCGAGGTGCGCGGCGGCG(-50 bp)GGCGTGCAGAAGACGCTCTCCAA(deletion)<br>(SEQ ID NO: 34) |
| T0-14 | wild-type | GCGCCGCGCGGTGGCGAGGGGCGTGC(26 bp)CTGGCCAACTTCCTCCCCACGGGCAC(wild-type)<br>(SEQ ID NO: 16) |
| T0-15 | homozygous | GTCCATGCTGGCCAACTTC(-6 bp;85 bp)ACGGGCACGCTGCTAACCTTC(deletion and insertion)<br>(SEQ ID NO: 35) |
| T0-16 | wild-type | GCGCCGCGCGGTGGCGAGGGGCGTGC(26 bp)CTGGCCAACTTCCTCCCCACGGGCAC(wild-type)<br>(SEQ ID NO: 16) |
| T0-17 | homozygous | CGGGGAAGGAAGCGCCGCGCT(-59 bp)CACGGGCACGCTGCTAACCT(substitution and deletion)<br>(SEQ ID NO: 36) |
| T0-18 | heterozygous | GCGCCGCGCGGTGGCGAGGGGCGTGC(26 bp)CTGGCCAACTTCCTCCCCACGGGCAC(wild-type)<br>(SEQ ID NO: 16) |
| T0-19 | wild-type | GCGCCGCGCGGTGGCGAGGGGCGTGC(26 bp)CTGGCCAACTTCCTCCCCACGGGCAC(wild-type)<br>(SEQ ID NO: 16) |
| T0-20 | homozygous | AGCGCCGCGCGGTGGCGAGGG(-54 bp)GCACGCTGCTAACCTTCGAGATG(deletion)<br>(SEQ ID NO: 37) |
| T0-21 | wild-type | GCGCCGCGCGGTGGCGAGGGGCGTGC(26 bp)CTGGCCAACTTCCTCCCCACGGGCAC(wild-type)<br>(SEQ ID NO: 16) |
| T0-22 | wild-type | GCGCCGCGCGGTGGCGAGGGGCGTGC(26 bp)CTGGCCAACTTCCTCCCCACGGGCAC(wild-type)<br>(SEQ ID NO: 16) |
| T0-23 | heterozygous | GCGCCGCGCGGTGGCGAGGGGCGTGC(26 bp)CTGGCCAACTTCCTCCCCACGGGCAC(wild-type)<br>(SEQ ID NO: 16) |
| T0-24 | heterozygous | GCGCCGCGCGGTGGCGAGGGGCGTGC(26 bp)CTGGCCAACTTCCTCCCCACGGGCAC(wild-type)<br>(SEQ ID NO: 16) |

The strain T0-8 of T0 generation transgenic maize with a homozygous mutation in ZmPLA1E gene contains the mutant ZmPLA1E gene in two homologous chromosomes, and the mutant ZmPLA1E gene is a DNA molecule obtained by deleting the bases at positions 168-226 from the ZmPLA1E gene (SEQ ID NO: 1) and keeping the other bases unchanged.

The strain T0-13 of the T0 generation transgenic maize with a homozygous mutation in ZmPLA1E gene contains the mutant ZmPLA1E gene in two homologous chromosomes, and the mutant ZmPLA1E gene is a DNA molecule obtained by deleting the bases at positions 127-176 from the ZmPLA1E gene (SEQ ID NO: 1) and keeping the other bases unchanged.

The strain T0-15 of the T0 generation transgenic maize with a homozygous mutation in ZmPLA1E gene contains the mutant ZmPLA1E gene in two homologous chromosomes, and the mutant ZmPLA1E gene is a DNA molecule obtained by deleting the bases at positions 222-227 from the ZmPLA1E gene (SEQ ID NO: 1) and inserting the following sequence of 85 bp into the deleted position: GAGATGCTACTCCAAGACGGGAGGAAGTTCTCCAAGGTTAGCATCTCCAAGAC GTCCATGCTGGCCAACGTCCATGCTCTCCAAG$_{(SEQ\ ID\ NO:\ 38)}$, and keeping the other bases unchanged.

The strain T0-17 of the T0 generation transgenic maize with a homozygous mutation in ZmPLA1E gene contains the mutant ZmPLA1E gene in two homologous chromosomes, and the mutant ZmPLA1E gene is a DNA molecule obtained by deleting the bases at positions 168-226 from the ZmPLA1E gene (SEQ ID NO: 1) and substituting the base G at position 167 with T, and keeping the other bases unchanged.

5) Genotype Identification of T1 Generation Transgenic Maize

The strains T0-8, T0-13, T0-15 and T0-17 of the T0 generation transgenic maize with a homozygous mutation in ZmPLA1E gene obtained in the step 4) were self-crossed, and the seeds were harvested and then sown to obtain T1 generation transgenic maize. The genotype of the ZmPLA1E gene of the T1 generation transgenic maize was identified, and the specific method was as follows: using the genomic DNA of the T1 generation transgenic maize as a template, and the primers ZmPLA1E_F and ZmPLA1E_R for detecting the mutant ZmPLA1E sequence were used to identify the genotype of the ZmPLA1E gene of the T1 generation transgenic maize according to the method in step 4). The results showed that all the T1 generation transgenic maize individual plants were consistent with the genotype of the previous generation. The strain T0-17 of the T1 generation transgenic maize with a homozygous mutation in ZmPLA1E gene was selected for the following haploid induction ability analysis experiment.

Figure 5:
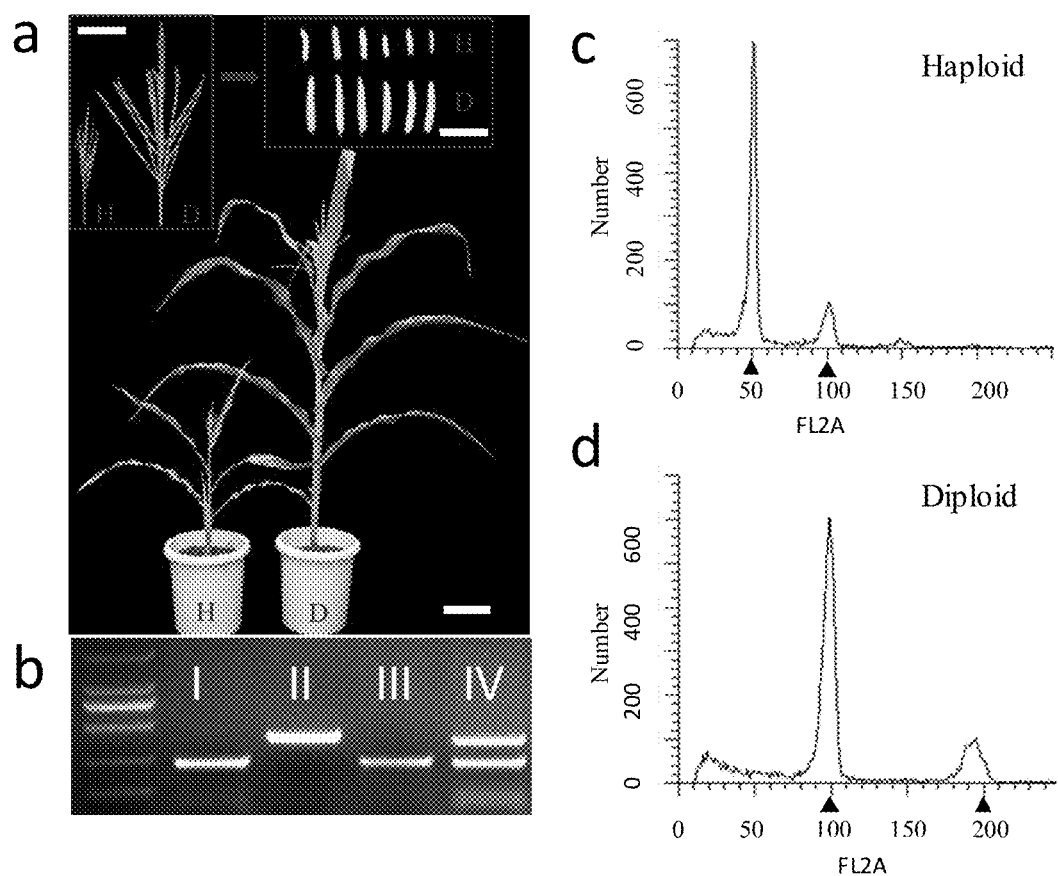
FIG. 5 shows the transgenic haploid phenotype verification. Figure a is a comparison of a haploid and a diploid on plants, tassels and anthers (H represents the haploid and D represents the diploid). Figure b is a molecular marker verification gel picture of a haploid and a diploid, I is the band type of the female parent material, II is the band type of the male parent material, III is the band type of the haploid, and IV is the band type of the diploid. Figure c is a signal diagram of the flow cytometry of a haploid plant. Figure d is a signal diagram of the flow cytometry of a diploid plant.

II. Identification of Haploid Induction Ability of Mutant Obtained by Knocking Out the ZmPLA1E Gene in Maize by CRISPR/Cas9 System 1. Phenotype Identification in Field The hybrid Zhengdan 958 (please see the literature "Du Chunxin, Cao Chunjing, Cao Qing, et al. The Breeding and Application of Maize hybrid Zhengdan 958 [J]. Maize Science, 2006, 14 (6): 43-45" or it can be obtained from ORIGIN AGRITECH LIMITED) was pollinated with the pollen of the strain T0-17 of the T1 generation transgenic maize with a homozygous mutation in ZmPLA1E gene obtained in step I, and the hybrid progeny was obtained; the resulting hybrid progeny were sown in the field, and the phenotype of the progeny was observed. The haploid had the characteristics of short plant, narrow and upswept leaves, compact plant type, male sterility, etc. The diploid was characterized by tall plant, wide leaves, scatter, normal fertility (FIG. 5a).

The progeny of the wild-type maize B104 and Zhengdan 958 were used as the control.

Six of the 5,080 hybrid progeny of the strain T0-17 of the T1 generation transgenic maize with a homozygous mutation in ZmPLA1E gene and the hybrid Zhengdan 958 were obtained as individual plants showing haploid traits, which were proposed to be haploid plants.

2. Leaf Ploidy Identification by Flow Cytometry

Flow cytometry was performed on the plants showing haploid traits obtained in above step 1 and the specific method was as follows: extracting the cell nuclei of the young leaves of the plant to be tested, using diploid maize leaves as the control; and detecting the signal by flow cytometry, first detecting the diploid cell nuclei signal, and setting the diploid cell nuclei signal peak to 100 (since the genetic material in the diploid cells is twice the genetic material in the haploid cells, the haploid cell nuclei signal peak appears near 50). If the cell nuclei signal peak of the plant to be tested appears near 50, the plant to be tested is considered to be a haploid plant (FIG. 5c). If the signal peak of the plant to be tested appears near 100, which is the same as the diploid cell nuclei signal intensity enrichment position (FIG. 5d), the plant to be tested is considered to be a diploid.

The results were as follows: after the six of the hybrid progeny of the T1 generation transgenic maize with a homozygous mutation in ZmPLA1E gene and hybrid Zhengdan 958 identified by phenotype identification to be candidate haploids were detected by flow cytometry, their ploidies showed that they were all haploids, named candidate haploid plants of the strains of the T1 generation transgenic maize with a homozygous mutation in ZmPLA1E gene.

3. Molecular Marker Identification

The genomic DNA of the candidate haploid plants of the strains of the T1 generation transgenic maize with a homozygous mutation in ZmPLA1E gene obtained in the above step 2 was extracted, and the polymorphic primers Chr4-222.7F (Chr4-222.7F: CACAAACTGGACAAAGTTGATGC$_{(SEQ\ ID\ NO:\ 39)}$) and Chr4-222.7R (Chr4-222.7R: TGACAACGCTTAAATGAACCTTGAT$_{(SEQ\ ID\ NO:\ 40)}$) between Zhengdan 958 and the strain T0-17 of the T1 generation transgenic maize with a homozygous mutation in ZmPLA1E gene were used to conduct PCR amplification, and the amplification products were subjected to agarose band test. If the amplification product of the individual plant to be tested is 250 bp, showing one band, it is considered that the band of the individual plant is Zhengdan 958 band type, and there is no band type of the parent material, and the individual plant is a maternal haploid. If the amplification products of the plant to be tested are 250 bp and 401 bp, showing two bands, it is considered that the band of the individual plant is a heterozygous band of Zhengdan 958 and the strain with a homozygous mutation in ZmPLA1E gene, and the plant is a progeny of normal hybrid and is a diploid.

The molecular marker identification results are as follows:

Molecular marker identification of the candidate haploid plants of the strains of the T1 generation transgenic maize with a homozygous mutation in ZmPLA1E gene showed that the candidate haploid plants of the strains of the T1 generation transgenic maize with a homozygous mutation in ZmPLA1E gene were all maternal haploid plants (FIG. 5b).

Therefore, in the progeny of the strain of the transgenic maize with a homozygous mutation in ZmPLA1E gene and the hybrid, if the plant is identified to be a haploid according to any one of the above three methods, the plant is a maize maternal haploid or a candidate maize maternal haploid; if the plant is identified to be a haploid according to none of the above three methods, the plant is not a maize maternal haploid or not a candidate maize maternal haploid.

The above identification results were collected and the induction rate was calculated according to the following formula: induction rate (%)=(number of maternal haploid plants/total number of plants)×100. As can be seen from Table 3, the maize maternal haploid can be obtained in the hybrid progeny of the material with a mutant ZmPLA1E gene and other materials.

TABLE 3

Statistics of haploid induction rate after mutation of ZmPLA1E gene

| Female parent | Male parent | Number of ears | Number of maternal haploids | Total number of plants | Haploid induction rate (%) |
|---|---|---|---|---|---|
| Zhengdan 958 | Wild-type | 8 | 0 | 4039 | 0.00 |
| | zmpla1e | 10 | 6 | 5080 | 0.12 | zmpla1e: the strain T0-17 of the T1 generation transgenic maize with a homozygous mutation in ZmPLA1E gene;
wild-type: wild-type maize B104

III. Application of the ZmPLA1E Gene Mutation in the Transgenic Maize in Improving Haploid Induction Ability The ZmPLA1 gene is also a very important haploid-inducing gene that has been cloned and reported (Chen, C. L. X. L. (2017). "A 4-bp Insertion at ZmPLA 1 Encoding a Putative Phospholipase A Generates Haploid Induction in Maize." Molecular Plant: English Edition 10 (3): 520-522.). In order to further increase the haploid induction rate, the haploid induction ability of the ZmPLA1E gene mutant was identified based on the ZmPLA1 mutation.

1. Acquisition of Double Gene-Mutant

The strains T0-15 and T0-17 of the T1 generation transgenic maize with a homozygous mutation in ZmPLA1E gene obtained in step I were respectively hybridized with the CAUHOI (CAUHOI is a parthenogenetic haploid-inducing line with an induction rate of 1-2%, and the ZmPLA1 gene has been mutated in this material) to obtain a F1. The obtained F1 was then self-crossed to obtain a F2 population. The F2 population was planted according to the families, and the genotypes of the ZmPLA1 gene and the ZmPLA1E gene of the individual plants of the F2 population were identified using primer pairs PLA1-F/PLA1-R, pla1-F/pla1-R and ZmPLA1E_F/ZmPLA1E_R, respectively. The individual plants with the following three genotypes were selected: homozygous mutation in ZmPLA1 gene and no mutation in ZmPLA1E gene; homozygous mutation in ZmPLA1 gene and heterozygous mutation in ZmPLA1E gene; homozygous mutation in ZmPLA1 gene and homozygous mutation in ZmPLA1E gene.

The sequence comparison of the wild-type ZmPLA1 gene and the mutant ZmPLA1 gene is shown in Table 4. The mutant ZmPLA1 gene has a 4 bp insertion in the 4th exon as compared to the wild-type ZmPLA1 gene. The 3' end of the F primer was designed to be at the position of the mutation using the kasp principle.

The sequences of the designed primers for detecting the genotype of the ZmPLA1 gene are as follows: PLA1-F: ACGTGGAGACAGGGAGGTAC$_{(SEQ\ ID\ NO:41)}$; PLA1-R: GTACGACGCACATCTAGAGCC$_{(SEQ\ ID\ NO:\ 42)}$. pla1-F: ACGTGGAGACAGGGAGCGAG$_{(SEQ\ ID\ NO:\ 43)}$; pla1-R: GCTTCTGGGGTTGATGGCAG$_{(SEQ\ ID\ NO:\ 44)}$.

Figure 6:
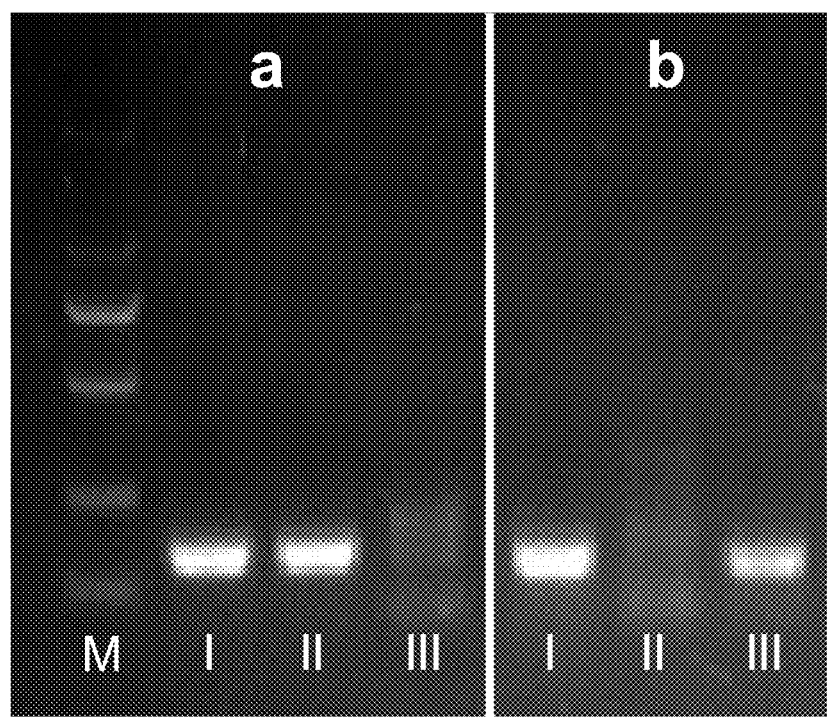
FIG. 6 shows the primers for detecting the ZmPLA1 gene mutation site. Figure a is the amplification bands of the primer pair of PLA1-F and PLA1-R. Figure b is the amplification bands of the primer pair of pla1-F and pla1-R. M is a 2K DNA marker; I is a heterozygous ZmPLA1 mutant; II is a homozygous ZmPLA1 wild-type plant; and III is a homozygous ZmPLA1 mutant.

The amplification bands of the primer pairs PLA1-F/PLA1-R and pla1-F/pla1-R are shown in FIG. 6. The primer pair PLA1-F and PLA1-R specifically amplified the wild-type ZmPLA1 band, i.e., the homozygous ZmPLA1 wild-type or heterozygous ZmPLA1 mutant had a band of 155 bp, while the homozygous ZmPLA1 mutant had no amplification band (FIG. 6a). The primer pair pla1-F and pla1-R specifically amplified the mutant ZmPLA1 band, i.e., the homozygous ZmPLA1 mutant or the heterozygous ZmPLA1 mutant had a band of 141 bp, while the homozygous ZmPLA1 wild-type had no amplification band (FIG. 6b). The ZmPLA1 genotype of the individual plant of the F2 population was identified by combining the amplification bands of the two primer pairs:

If an amplification band of 155 bp is obtained using the primer pair PLA1-F/PLA1-R, and no amplification band is obtained using the primer pair pla1-F/pla1-R, the genotype of the individual plant is homozygous ZmPLA1 wild-type;

If no amplification band is obtained using the primer pair PLA1-F/PLA1-R, and an amplification band of 141 bp is obtained using the primer pair pla1-F/pla1-R, the genotype of the individual plant is homozygous ZmPLA1 mutant;

If an amplification band of 155 bp is obtained using the primer pair PLA1-F/PLA1-R, and an amplification band of 141 bp is obtained using the primer pair pla1-F/pla1-R, the genotype of the individual plant is heterozygous ZmPLA1 mutant.

The method of identifying the genotype of the ZmPLA1E gene of the individual plant of the F2 population by using ZmPLA1E_F/ZmPLA1E_R was the same as above.

The mutant ZmPLA1 gene and the wild-type ZmPLA1E gene were both contained in the two homologous chromosomes of the plant whose genotype was a homozygous ZmPLA1 mutant and not a ZmPLA1E mutant. The mutant ZmPLA1 gene was a DNA molecule obtained by substituting the base C at position 409 of the ZmPLA1 gene (SEQ ID NO: 7) with T, and substituting the base C at position 421 with G, and substituting the base T at position 441 with C, and substituting the base T at position 887 with G, and substituting the base G at position 1210 with C, and substituting the base T at position 1306 with C, and substituting the base G at position 1435 with A, and substituting the base C at position 1471 with A, and substituting the base A at position 1541 with C, and inserting the base sequence "CGAG" of 4 bp at position 1572, and substituting the base T at position 1588 with C, and substituting the base C at position 1591 with A and keeping other bases unchanged.

TABLE 4

Sequence comparison of wild-type ZmPLA1 and mutant ZmPLA1

| Position (starting from 5' UTR) | Type | Nucleotide | |
|---|---|---|---|
| | | Wild-type ZmPLA1 | Mutant ZmPLA1 |
| 409 | SNP | C | T |
| 421 | SNP | C | G |
| 441 | SNP | T | C |
| 887 | SNP | T | G |
| 1210 | SNP | G | C |
| 1306 | SNP | T | C |
| 1435 | SNP | G | A |
| 1471 | SNP | C | A |
| 1541 | SNP | A | C |

TABLE 4-continued

Sequence comparison of wild-type ZmPLA1 and mutant ZmPLA1

| Position (starting from 5' UTR) | Type | Nucleotide | |
|---|---|---|---|
| | | Wild-type ZmPLA1 | Mutant ZmPLA1 |
| 1572 | Insertion | | CGAG |
| 1588 | SNP | T | C |
| 1591 | SNP | C | A |

The above mutant ZmPLA1 gene (the mutant ZmPLA1 gene in the plant whose genotype was a homozygous ZmPLA1 mutant and not a ZmPLA1E mutant) was contained in the two homologous chromosomes of the plant whose genotype was homozygous ZmPLA1 gene mutant and heterozygous ZmPLA1E gene mutant. The mutant ZmPLA1E gene was contained in one homologous chromosome of the plant whose genotype was homozygous ZmPLA1 gene mutant and heterozygous ZmPLA1E gene mutant, and the mutant ZmPLA1E gene was a DNA molecule obtained by deleting the bases at position 168-226 from the ZmPLA1 gene (SEQ ID NO: 1), and substituting the base G at position 167 with T, and keeping other bases unchanged, while the other homologous chromosome contained wild-type ZmPLA1E gene.

The above mutant ZmPLA1 gene (the mutant ZmPLA1 gene in the plant whose genotype was a homozygous ZmPLA1 mutant and not a ZmPLA1E mutant) and the above mutant ZmPLA1E gene (the mutant ZmPLA1E gene in the plant whose genotype was a homozygous ZmPLA1 gene mutation and heterozygous ZmPLA1E gene mutation) were both contained in the two homologous chromosomes of the plant whose genotype was homozygous ZmPLA1 gene mutant and homozygous ZmPLA1E gene mutant.

2. Phenotype Identification in Field

Figure 4:
FIG. 4 shows the phenotypes of transgenic ears. Left: homozygous mutation in ZmPLA1 gene and no mutation in ZmPLA1E gene; middle: homozygous mutation in ZmPLA1 gene and heterozygous mutation in ZmPLA1E gene; right: homozygous mutation in ZmPLA1 gene and homozygous mutation in ZmPLA1E gene.

The hybrid Zhengdan 958 was pollinated with the pollen of the individual plants with the three genotypes obtained in step 1 respectively and the hybrid ears are shown in FIG. 4.

The resulting hybrid progeny were sown in the field, and the phenotype of the progeny was observed. The haploid had the characteristics of short plant, narrow and upswept leaves, compact plant type, male sterility, etc. The diploid was characterized by tall plant, wide leaves, scatter, normal fertility.

Among the 5888 hybrid progeny of the plant whose genotype was a homozygous ZmPLA1 gene mutant and not a ZmPLA1E gene mutant and the hybrid Zhengdan 958, 47 hybrid progeny were obtained as individual plants showing haploid traits, which were proposed to be haploid plants.

Among the 5527 hybrid progeny of the plant whose genotype was a homozygous ZmPLA1 gene mutant and a heterozygous ZmPLA1E gene mutant and the hybrid Zhengdan 958, 179 hybrid progeny were obtained as individual plants showing haploid traits, which were proposed to be haploid plants.

Among the 3161 hybrid progeny of the plant whose genotype was a homozygous ZmPLA1 gene mutant and a homozygous ZmPLA1E gene mutant and the hybrid Zhengdan 958, 244 hybrid progeny were obtained as individual plants showing haploid traits, which were proposed to be haploid plants.

3. Leaf Ploidy Identification by Flow Cytometry

The above haploid individual plants were subjected to flow cytometry according to the method of the substep 2 in the step II. The results showed that the ploidies of the haploid individual plants proposed in step 2 were all haploids.

4. Molecular Marker Identification

The above haploid individual plants were subjected to molecular marker identification according to the method of substep 3 in the step II. The results showed that the ploidies of the haploid plants proposed in step 2 were all haploids.

Therefore, in the progeny of the plants having the above three genotypes and the hybrid, if the plant is identified to be a haploid according to any one of the above three methods, the plant is a maize maternal haploid or a candidate maize maternal haploid; if the plant is identified to be a haploid according to none of the above three methods, the plant is not a maize maternal haploid or not a candidate maize maternal haploid.

The above identification results were collected and the induction rate was calculated according to the following formula: induction rate (%)=(number of maternal haploid plants/total number of plants)×100. It can be seen from Table 5 that on the basis of the homozygous mutation of ZmPLA1 gene, the maize maternal haploid can be obtained in the hybrid progeny of the material with a mutant ZmPLA1E gene and other materials and the haploid induction rate is significantly increased, indicating that the ZmPLA1E gene mutation can significantly increase the haploid induction rate.

TABLE 5

Statistics of haploid induction rate of the hybrid progeny of the ZmPLA1E gene mutants and the CAUHOI

| Female parent | Male parent | Number of ears | Number of maternal haploids | Total number of plants | Haploid induction rate (%) |
|---|---|---|---|---|---|
| Zhengdan 958 | A | 14 | 47 | 5888 | 0.80 |
| | H | 20 | 179 | 5527 | 3.24 |
| | B | 20 | 244 | 3161 | 7.72 |

Note:
A: plant whose genotype is a homozygous ZmPLA1 gene mutant and not a ZmPLA1E gene mutant; H: plant whose genotype is a homozygous ZmPLA1 gene mutant and a heterozygous ZmPLA1E gene mutant; B: plant whose genotype is a homozygous ZmPLA1 gene mutant and a homozygous ZmPLA1E gene mutant.

INDUSTRIAL APPLICATION

The present invention cloned the parthenogenetic haploid-inducing gene ZmPLA1E from maize. Experiments have shown that mutations in ZmPLA1E can produce and significantly increase parthenogenetic haploid induction ability, which is of great significance in the selection of novel inducing lines, further improvement of induction rate, and improvement of the efficiency of maize haploid breeding. The present invention lays an important foundation for revealing the genetic and biological mechanisms of the generation of the maize parthenogenetic haploid. In view of the extensive use of haploid breeding technology in the breeding industry at present, the present invention has a very wide application space and market prospect.

What is claimed is:

1. A method for preparing a plant maternal haploid-inducing line, comprising the following steps:
   silencing or inhibiting the expression and/or activity of the ZmPLA1E gene in the genome of a target plant or knocking out the ZmPLA1E gene to obtain a transgenic plant, i.e., the plant maternal haploid-inducing line
   wherein said ZmPLA1E gene encodes a protein comprising at least 95% sequence identity to SEQ ID NO. 3.

2. The method according to claim 1, wherein the silencing or inhibiting the expression and/or activity of the ZmPLA1E gene in the genome of the target plant or knocking out the ZmPLA1E gene is mutating the ZmPLA1E gene in the genome of the target plant to reduce the expression level of the ZmPLA1E gene in the genome of the target plant or cause a deletion mutation, insertion mutation or base substitution of the ZmPLA1E gene in the genome of the target plant.

3. The method according to claim 2, wherein the method of causing a deletion mutation, insertion mutation or base substitution of the ZmPLA1E gene in the genome of the target plant can be CRISPR/Cas9.

4. The method according to claim 3, wherein the target sequence of the CRISPR/Cas9 is positions 163-182 or 210-229 of SEQ ID NO: 1.

5. The method according to claim 3, wherein the sgRNA sequence of the CRISPR/Cas9 is SEQ ID NO: 6.

6. The method according to claim 1, wherein the target plant is maize.

7. The method according to claim 1, wherein the method further comprising: silencing or inhibiting the expression and/or activity of the ZmPLA1 gene in the genome of a target plant or knocking out the ZmPLA1 gene.

8. A plant maternal haploid-inducing line, in which the expression and/or activity of ZmPLA1E gene in the genome of said plant is silenced or inhibited, or the ZmPLA1E gene in the genome of said plant is knocked out;
   Wherein, said ZmPLA1E gene encodes a protein comprising at least 95% sequence identity to SEQ ID NO.3.

9. The plant maternal haploid-inducing line according to claim 8, wherein, in said plant maternal haploid-inducing line, the expression and/or activity of ZmPLA1 gene is silenced or inhibited, or the ZmPLA1 gene is knocked out.

10. The plant maternal haploid-inducing line according to claim 8, wherein the plant including the whole plant, root, stem, leaf, flower, fruit, seed, or pollen.

11. The plant maternal haploid-inducing line according to claim 8, wherein the plant is maize.

12. A method for preparing a plant maternal haploid, comprising the following steps: self-crossing the plant maternal haploid-inducing line according to claim 8 or a progeny thereof or hybridizing it as a male parent with other plant materials, to obtain a self-crossed progeny or hybrid progeny, i.e., the plant maternal haploid.

13. The method according to claim 12, wherein the method further comprises the following steps:
   conducting haploid trait identification, leaf ploidy identification and/or molecular marker identification on the self-crossed progeny or hybrid progeny; and
   selecting the progeny identified as a haploid by at least one method to be the plant maternal haploid.

14. The method according to claim 12, wherein the plant is maize.

* * * * *